(12) United States Patent
Seemann et al.

(10) Patent No.: US 12,201,377 B2
(45) Date of Patent: Jan. 21, 2025

(54) ARM MOVEMENT SAFETY LAYER

(71) Applicant: Mazor Robotics Ltd., Caesarea (IL)

(72) Inventors: Ziv Seemann, Beit Ytzhack (IL); Gal Barazani, Haifa (IL); Ori Ben Zeev, Ramat HaSharon (IL); Dvir Kadshai, Tel Aviv (IL); Itamar Eshel, Tzur Igal (IL)

(73) Assignee: Mazor Robotics Ltd., Caesarea (IL)

( * ) Notice: Subject to any disclaimer, the term of this patent is extended or adjusted under 35 U.S.C. 154(b) by 475 days.

(21) Appl. No.: 17/516,408

(22) Filed: Nov. 1, 2021

(65) Prior Publication Data
US 2023/0133689 A1    May 4, 2023

(51) Int. Cl.
*A61B 34/20* (2016.01)
*A61B 34/00* (2016.01)
*A61B 34/30* (2016.01)

(52) U.S. Cl.
CPC .............. *A61B 34/20* (2016.02); *A61B 34/30* (2016.02); *A61B 34/77* (2016.02); *A61B 2034/2048* (2016.02); *A61B 2034/2059* (2016.02)

(58) Field of Classification Search
CPC ......... A61B 34/20; A61B 34/30; A61B 34/77; A61B 2034/2048; A61B 2034/2059; A61B 2090/064; B25J 9/1674; B25J 9/1694; G05B 2219/37357; G05B 2219/37374; G05B 2219/40223; G05B 2219/40228; G05B 2219/37024; G05B 2219/37324; G05B 2219/37388; G05B 2219/45117
See application file for complete search history.

(56) References Cited

U.S. PATENT DOCUMENTS

| | | | |
|---|---|---|---|
| 11,096,753 B1 | 8/2021 | Mantri et al. | |
| 2005/0264251 A1 | 12/2005 | Bischoff et al. | |
| 2010/0332032 A1* | 12/2010 | Moriyama | B25J 9/1633 700/258 |
| 2016/0136812 A1 | 5/2016 | Hosek et al. | |
| 2017/0182666 A1 | 6/2017 | Szarski et al. | |
| 2020/0241536 A1 | 7/2020 | Liu et al. | |
| 2021/0401521 A1* | 12/2021 | Mantri | A61B 90/37 |

FOREIGN PATENT DOCUMENTS

| | | | |
|---|---|---|---|
| JP | 2011-042022 | | 3/2011 |
| JP | 2011042022 A | * | 3/2011 |
| WO | WO 2020/160388 | | 8/2020 |

OTHER PUBLICATIONS

JP 2011042022A translation (Year: 2011).*
International Search Report and Written Opinion for International (PCT) Patent Application No. PCT/IL2022/051148, dated Feb. 20, 2023, 14 pages.

* cited by examiner

*Primary Examiner* — Ian Jen
*Assistant Examiner* — Renee LaRose
(74) *Attorney, Agent, or Firm* — Sheridan Ross P.C.

(57) ABSTRACT

A system according to at least one embodiment of the present disclosure includes a processor; and at least one inertial sensor having a known physical relationship with a tracked object in a first pose, the at least one inertial sensor providing a measurement indicative of a movement of the tracked object from the first pose to a second pose, wherein the processor determines the second pose of the tracked object based, at least in part, on the measurement provided by the at least one inertial sensor.

20 Claims, 6 Drawing Sheets

ARM MOVEMENT SAFETY LAYER

FIELD

The present technology generally relates to motion detection and relates more particularly to using inertial sensors to detect motion.

BACKGROUND

Surgical robots may assist a surgeon or other medical provider in carrying out a surgical procedure, or may complete one or more surgical procedures autonomously. Robotic arms may be used semi-autonomously or autonomously in a surgery.

SUMMARY

Example aspects of the present disclosure include:

A system according to at least one embodiment of the present disclosure comprises: a processor; and at least one inertial sensor having a known physical relationship with a tracked object in a first pose, the at least one inertial sensor providing a measurement indicative of a movement of the tracked object from the first pose to a second pose, wherein the processor determines the second pose of the tracked object based, at least in part, on the measurement provided by the at least one inertial sensor.

Any of the aspects herein, wherein the movement of the tracked object is caused by a force applied to the tracked object, and wherein the processor determines a difference between the first pose and the second pose.

Any of the aspects herein, wherein the processor generates, when the difference between the first pose and the second pose is greater than a threshold value, an alert.

Any of the aspects herein, wherein the tracked object comprises a robot, and wherein the at least one inertial sensor comprises a plurality of sensors disposed on one or more locations of the robot.

Any of the aspects herein, wherein the one or more locations of the robot comprise at least one of one or more joints of the robot, one or more cantilevers of the robot, a height adjustment device mechanically coupled with the robot, or a shoulder of the robot.

Any of the aspects herein, wherein the robot comprises a plurality of cantilevers, and wherein the movement of the robot from the first pose to the second pose comprises at least one cantilever of the plurality of cantilevers deflecting from a first position to a second position.

Any of the aspects herein, wherein the at least one inertial sensor comprises a force sensor, and wherein the force sensor measures a force on the tracked object.

A system according to at least one embodiment of the present disclosure comprises: a processor; a tracked object oriented in a first pose; and an inertial measurement unit disposed in a known physical relation to the tracked object, the inertial measurement unit producing a first reading indicating a change in pose of the tracked object, wherein the processor determines a second pose of the tracked object based at least in part on the first reading provided by the inertial measurement unit.

Any of the aspects herein, wherein the system further comprises: one or more encoders disposed on the tracked object, the one or more encoders providing a measurement of the change in pose of the tracked object independent of the first reading.

Any of the aspects herein, wherein the processor determines a third pose based on the measurement from the one or more encoders, and wherein the processor determines a difference between the second pose to the third pose.

Any of the aspects herein, wherein the processor generates, when the difference between the second pose and the third pose exceeds a threshold value, an alert.

Any of the aspects herein, wherein the inertial measurement unit is disposed on the tracked object, wherein the inertial measurement unit comprises a force sensor, and wherein the inertial measurement unit generates a second reading measuring a force on the tracked object.

Any of the aspects herein, wherein the processor generates, when the measured force exceeds a threshold value, an alert.

Any of the aspects herein, wherein the tracked object comprises a cantilever, and wherein the force is applied to one or more portions of the cantilever.

A method according to at least one embodiment of the present disclosure comprises: receiving, from a first sensor coupled with a tracked object, a first sensor reading; determining, based at least in part on the first sensor reading, a first pose of the tracked object; receiving, from a second sensor coupled with the tracked object, a second sensor reading indicating the tracked object has changed pose from the first pose to a second pose; and determining, based on the second sensor reading, a second pose of the tracked object.

Any of the aspects herein, wherein the first sensor comprises an encoder, wherein the second sensor comprises a plurality of inertial sensors disposed on one or more locations of the tracked object, and wherein the method further comprises: receiving, from the encoder, a third reading related to the change in pose of the tracked object; determining, based on the third reading, a third pose of the tracked object; comparing the second pose to the third pose; and determining, based on the comparison of the second pose to the third pose, a difference between the second pose and the third pose.

Any of the aspects herein, further comprising: generating, when the difference between the second pose and the third pose is above a first threshold value, a first alert.

Any of the aspects herein, wherein the tracked object comprises a robot having a first cantilever, wherein the change in pose of the robot is caused at least in part by a force applied to the first cantilever to cause the first cantilever to move from a first position to a second position, and wherein the method further comprises: receiving, from a force sensor, a measurement of the force on the first cantilever; and generating, when the force on the first cantilever exceeds a second threshold value, a second alert.

Any of the aspects herein, wherein the tracked object comprises a robotic arm, and wherein the method further comprises: registering, based on the second pose, one or more portions of the robotic arm to a patient; and causing, based on the registration, the robotic arm to move relative to the patient.

Any of the aspects herein, wherein the one or more locations comprises at least one of one or more joints of the robot, a height adjustment device mechanically coupled to the robot, one or more cantilevers of the robot, or a shoulder of the robot.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Robots and/or robotic arms may use encoders to determine their position in space (e.g., kinematics). However, the encoders may have difficulty detecting deflections in one or more portions of the robot or robotic arm (e.g., an arm body), which may result in inaccuracies when determining the position of an end effector of the arm body. This inaccuracy may result in overall surgical inaccuracy (e.g., inaccuracy of an end effector holding a drill that drills into a spine vertebra). Further, deflections across multiple portions of the robot or robotic arm (e.g., deflections across multiple arm bodies) may be increased/cumulative (e.g., added, accumulated, multiplied, etc.) due to angular deflection and actual movement of the robotic arm (and/or tools attached thereto), which may compound the error associated with the position of the robotic arm. The deflection may also occur in other areas in the surgical environment, such as deflections between the bed mounting platform and the surgical bed, bending of the surgical bed due to force thereon, an angle change between the surgical bed and the floor, rigidity in the positioning system of the robot or robotic arm, rigidity of the shoulder of the robot or robotic arm, combinations thereof, and/or the like. Similarly, the weight of the robot or robotic arm itself may cause deflections thereof when compared to the "world" coordinate system (e.g., the coordinate system associated with the surgical environment).

A system according to embodiments of the present disclosure may include the addition of an accurate inertial unit (e.g., inertial sensors) along one or more of the joints of the robot or robotic arm, a height adjustment device, and a shoulder of the robot or robotic arm. The placement of the inertial unit may be easier to place on the robot motor driver since the driver is spread across the joints, or otherwise supported by multiple joints. The inertial unit(s) may then be zeroed, such that movement in the components on which the inertial units are disposed may be detected. In some embodiments, the zeroing of the inertial units may permit for the inertial unit to act as a compass to enable the system to determine when the robotic arm is not in the correct pose. The sensors may be used to learn the current position of the robotic arm and compare with the kinematics (e.g., determined by the encoders).

Embodiments of the present disclosure provide technical solutions to one or more of the problems of (1) deflections of robotic arms that are not captured by encoders, and/or (2) pose errors associated with one or more components of robotic arms.

Figure 1:
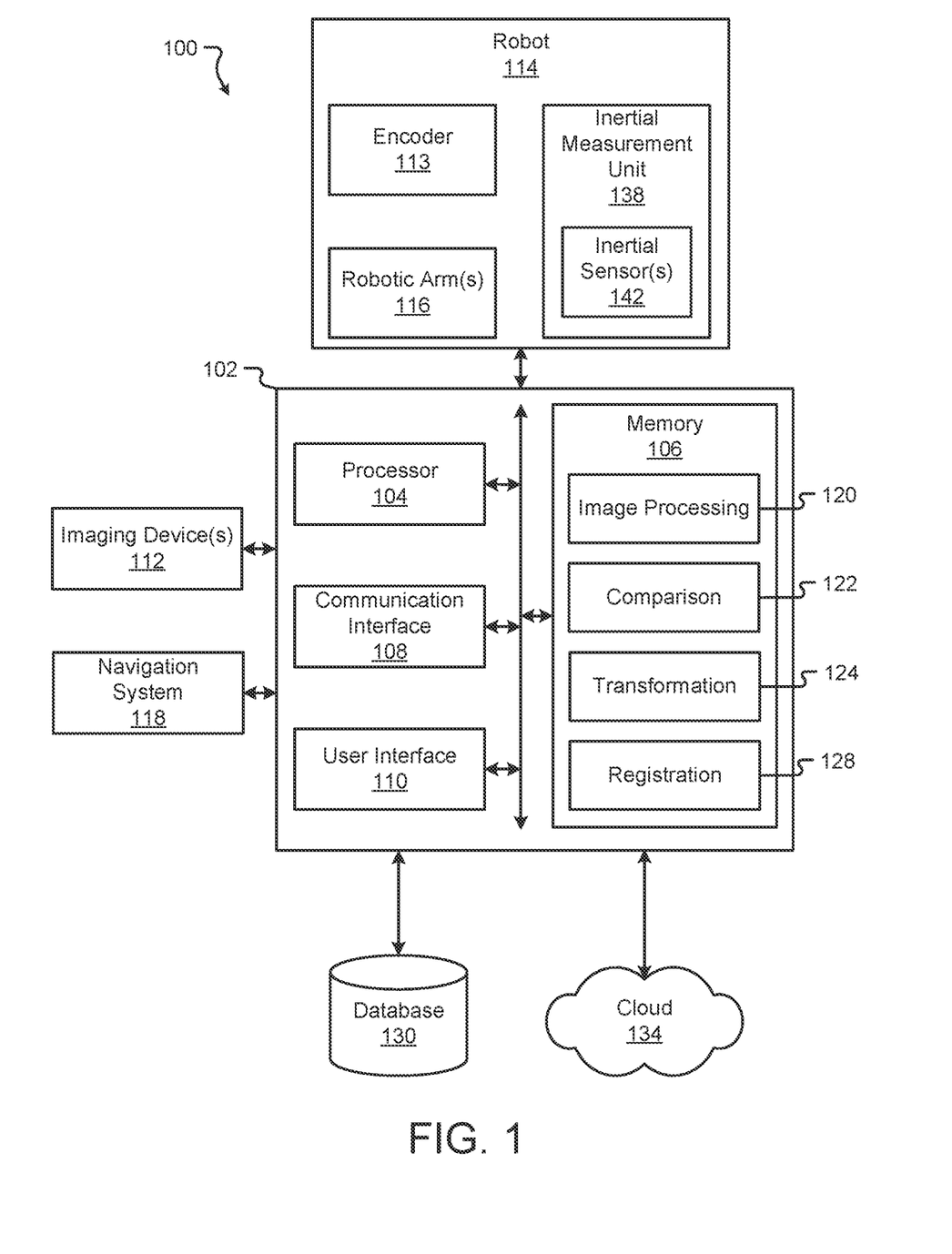
FIG. 1 is a block diagram of a system according to at least one embodiment of the present disclosure.

Turning first to FIG. 1, a block diagram of a system 100 according to at least one embodiment of the present disclosure is shown. The system 100 may be used to facilitate the performance of a surgery or surgical procedure; to detect deflections or bends in one or more components thereof during the surgery or surgical procedure; to verify the accuracy of one or more sensors; to detect excessive forces on one or more components thereof; and/or carry out one or more other aspects of one or more of the methods disclosed herein. In some embodiments, the system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

In some embodiments, the computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions, machine learning models, etc. stored in the memory 106, which may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300, 400, and/or 500 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120, comparison 122, transformation 124, and/or registration 128. Such content, if provided as an instruction, may, in some embodiments, be organized into one or more applications, modules, packages, layers, or engines.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor XTM Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors 142 that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example). In some embodiments, the arm(s) 116 may be mounted to an operating table, a separate table (e.g., a table proximate the operating table), the floor, the wall(s) of the operating room, the ceiling, combinations thereof, and/or other area in the surgical environment.

The robot 114 may comprise one or more encoders 113. The encoders 113 may be or comprise sensors which detect movements and produce signals or other data related thereto. In some embodiments, the encoders 113 may be or comprise absolute encoders (e.g., encoders that do not rely on previous position readings to determine a current position or that determine an absolute position), incremental encoders (e.g., encoders that report changes in position relative to a previous position), combinations thereof, and/or the like. The encoders 113 may be or comprise mechanical encoders (e.g., a potentiometer), optical encoders (e.g., a device that uses light sensors to detect light passing through a slit in a rotating disk), a magnetic encoder (e.g., a device that measures changes in magnetic field distribution created by movement of a motor), an electromagnetic induction encoder (e.g., a device that measures changes in magnetic fields generated between one or more induction coils and a fixed coil), combinations thereof, and/or the like. The encoders 113 may comprise linear encoders (e.g., encoders that detect linear position(s) or linear positional change(s) and produce signals or other data related thereto) and/or rotary encoders (e.g., encoders that detect rotary position(s) or rotary positional change(s) and produce signals or other data related thereto). The encoders 113 may have a known physical relationship (e.g., a fixed distance away from, proximate to, disposed on, etc.) with the robot 114, the robotic arm 116 (and/or one or more components thereof), the navigation system 118, combinations thereof, and/or the like. In one embodiment, the encoders 113 are disposed on the robot 114 and/or one or more components thereof (e.g., one or more portions of the robotic arms 116, one or more surgical mounting portions that connect the robot 114 to a surgical bed, a motor that controls motions of a robotic arm 116, etc.).

The robot 114 may comprise one or more inertial measurement units 138. The inertial measurement unit 138 may measure forces, angular rates, and/or orientation changes to itself or to the component to which the inertial measurement unit 138 is attached. For instance, the inertial measurement unit 138 may register a rotation of an object (e.g., a robotic arm) to which the inertial measurement unit 138 is attached when the object rotates. In some embodiments, the inertial measurement unit 138 may comprise one or more inertial sensors 142. The inertial sensors 142 may be or comprise accelerometers, gyroscopes, magnetometers, and/or other components for detecting movement of the inertial measurement unit 138. In some embodiments, the inertial measurement unit 138 may comprise one or more force sensors. The one or more force sensors may be capable of measuring direct or indirect force thereon and provide readings indicative of the magnitude and/or direction of the force.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (e.g., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 300, 400, and/or 500 described herein. The system 100 or similar systems may also be used for other purposes.

Figure 2A:
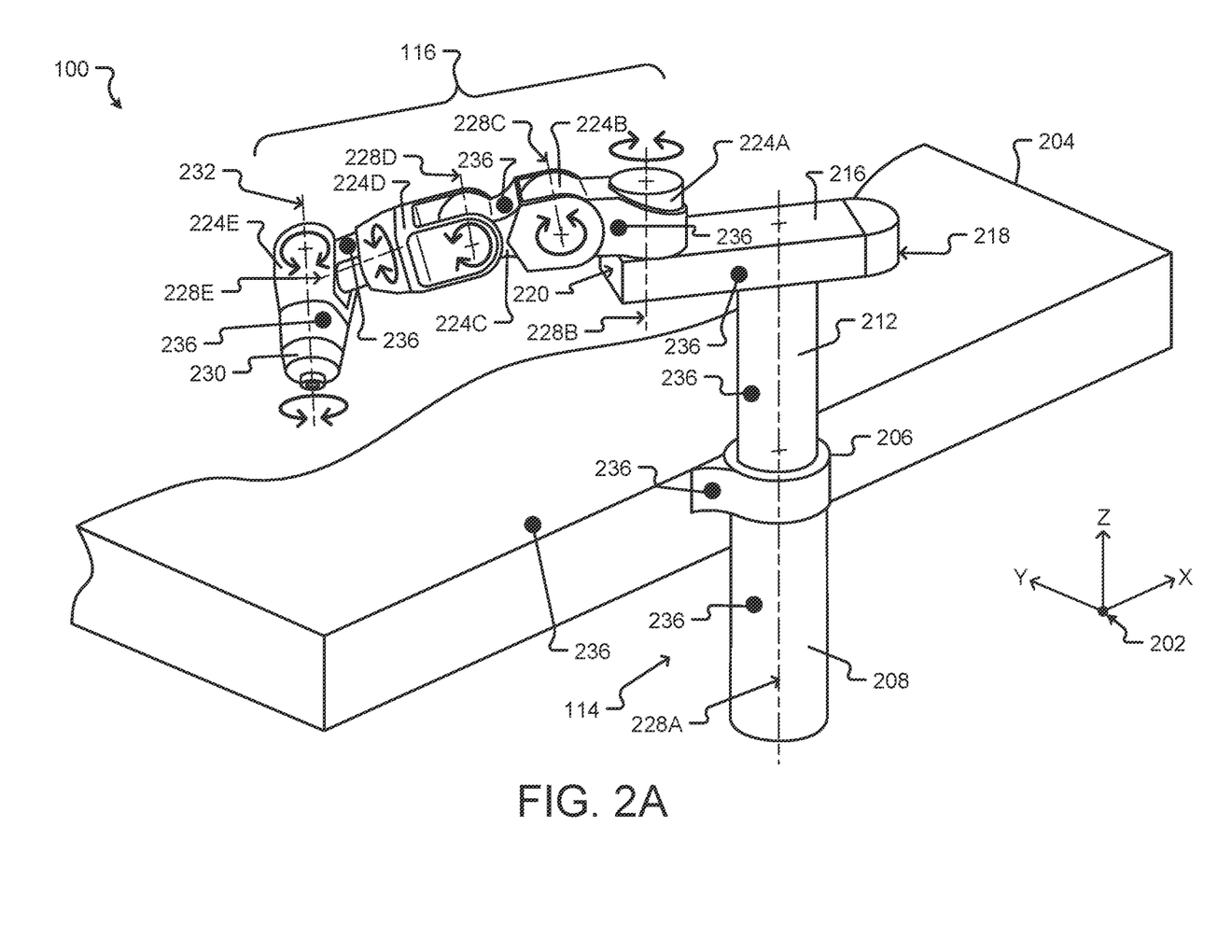
FIG. 2A is a schematic of a robotic arm according to at least one embodiment of the present disclosure.

FIG. 2A depicts aspects of the system 100 in accordance with embodiments of the present disclosure. The schematic of FIG. 2A depicts a robot 114 (and robotic arm 116 thereof) attached to a surgical bed 204. The surgical bed may be a flat, horizontal surface on which a patient may rest during the course of a surgery or surgical procedure. While FIG. 2A depicts the robot 114 mounted to a side of the surgical bed 204, the robot 114 may be mounted to other areas on the surgical environment (e.g., a rail system proximate the surgical bed 204, an apparatus separate from the surgical bed 204, etc.).

The robot 114 and/or the robotic arm 116 may be attached to the surgical bed 204 by an attachment mechanism 206. The attachment mechanism 206 may connect the robot 114 to a first side of the surgical bed 204 such that the robotic arm 116 can access a working volume or other area during a surgery or surgical procedure. The robot 114 may comprise a base 208 that contacts a floor or other support structure in the surgical environment to provide additional support to the robot 114. In some embodiments, the base 208 may be rotatable about an axis of rotation 228A that runs along a height direction of the base 208 (e.g., in the Z-axis direction of the coordinate system 202). The robot 114 may comprise a height adjustment device 212 that may be mechanically coupled with the attachment mechanism 206, the base 208, and/or the robotic arm 116. The height adjustment device 212 may be configured to move to adjust the height (e.g., the position in the Z-axis direction) of the robotic arm 116 (and/or components thereof). For instance, the height adjustment device 212 may retract into a hollow section of the base 208, such that the robotic arm 116 moves in the negative Z-axis direction (e.g., closer to the surgical bed 204 in the height direction). Similarly, the height adjustment device 212 may extend from the hollow section of the base 208 such that the robotic arm 116 moves in the Z-axis direction (e.g., further from the surgical bed 204 in the height direction).

The height adjustment device 212 may connect to a shoulder 216 of the robotic arm 116. The shoulder 216 may extend from a first end 218 to a second end 220. In some embodiments, the first end 218 may be a proximal end (e.g., an end further from the patient and closer to the surgeon) and the second end 220 may be a distal end (e.g., an end closer to the patient and further from the surgeon). The shoulder 216 may support the robotic arm 116 and/or one or more components thereof during the course of a surgery or surgical procedure. In some embodiments, the shoulder 216 may comprise one or more components of the system 100 (e.g., the navigation system 118). The shoulder 216 may be equipped with one or more motors (not shown), which may be activated or deactivated by the system 100 or components thereof (e.g., the computing device 102, the processor 104, etc.) to cause the robotic arm 116 to rotate about the axis of rotation 228A.

The shoulder 216 may comprise a cantilever 224A. The cantilever 224A may extend in the height direction (e.g., the Z-axis direction) with respect to the shoulder 216, and provide a surface or other structure to which other components of the robotic arm 116 can attach. For instance, as depicted in FIG. 2A, the cantilever 224A may be a cylindrical object projecting from the shoulder 216. In some embodiments, the cantilever 224A may be positioned closer to the second end 220 of the shoulder 216 than to the first end 218 of the shoulder 216. The cantilever 224A may be attached to or otherwise mechanically coupled with the shoulder 216 such that the cantilever 224A moves with the shoulder 216.

The cantilever 224A may be connected to or otherwise mechanically coupled with a cantilever 224B. The cantilever 224B may be rotatable with respect to an axis of rotation 228B (which may be an axis of rotation associated with the cantilever 224A), such that the cantilever 224B can rotate about one or more portions of the cantilever 224A. In some embodiments, a joint may be formed between the cantilever 224A and the cantilever 224B, such that the cantilever 224B can move with respect to the cantilever 224A (and vice versa). The joint may be a pin joint, a prismatic joint, a ball joint, a knuckle joint, a cotter joint, or the like. In some embodiments, the joint between the cantilevers 224A and 224B may comprise one or more bolts, screws, or other affixing mechanisms to mechanically couple the cantilever 224A with the cantilever 224B. In some embodiments, the cantilever 224A and/or the cantilever 224B may comprise brakes or other locking mechanisms that prevent the cantilever 224A from moving and/or rotating in one or more directions with respect to the cantilever 224B (or vice versa). For instance, the cantilever 224B may include one or more latches (not shown) that may lock the cantilever 224B in place relative to the cantilever 224A.

The cantilever 224B may be connected to or otherwise mechanically coupled with a cantilever 224C. The cantilever 224C may be rotatable with respect to an axis of rotation 228C. The rotatability of cantilever 224C may permit the cantilever 224C to rotate about one or more portions of the cantilever 224B. In some embodiments, one or more joints may connect the cantilever 224C to the cantilever 224B. The one or more joints may be pin joints, prismatic joints, ball joints, knuckle joints, cotter joints, or the like. In some embodiments, the joint between the cantilevers 224B and 224C may comprise one or more bolts, screws, or other affixing mechanisms to mechanically couple the cantilever 224C with the cantilever 224B. In some embodiments, the connection and/or movement relationship between the cantilever 224C and the cantilever 224B may be similar to or the same as the connection and/or movement relationship between the cantilever 224B and the cantilever 224A.

The cantilever 224C may be connected to or otherwise mechanically coupled with a cantilever 224D. The cantilever 224D may be rotatable with respect to an axis of rotation 228D. The rotatability of cantilever 224D may permit the cantilever 224D to rotate about one or more portions of the cantilever 224C. In some embodiments, one or more joints may connect the cantilever 224D to the cantilever 224C. The one or more joints may be pin joints, prismatic joints, ball joints, knuckle joints, cotter joints, or the like. In some embodiments, the joint between the cantilevers 224C and 224D may comprise one or more bolts, screws, or other affixing mechanisms to mechanically couple the cantilever 224D with the cantilever 224C. In some embodiments, the connection and/or movement relationship between the cantilever 224D and the cantilever 224C may be similar to or the same as the connection and/or movement relationship between the cantilever 224C and the cantilever 224B.

The cantilever 224C may be connected to or otherwise mechanically coupled with a cantilever 224D. The cantilever 224D may be rotatable with respect to an axis of rotation 228D. The rotatability of cantilever 224D may permit the cantilever 224D to rotate about one or more portions of the cantilever 224C. In some embodiments, one or more joints may connect the cantilever 224D to the cantilever 224C. The one or more joints may be pin joints, prismatic joints, ball joints, knuckle joints, cotter joints, or the like. In some embodiments, the joint between the cantilevers 224C and 224D may comprise one or more bolts, screws, or other affixing mechanisms to mechanically couple the cantilever 224D with the cantilever 224C. In some embodiments, the connection and/or movement relationship between the cantilever 224D and the cantilever 224C may be similar to or the same as the connection and/or movement relationship between the cantilever 224C and the cantilever 224B.

The cantilever 224D may be connected to or otherwise mechanically coupled with a cantilever 224E. The cantilever 224E may be rotatable with respect to an axis of rotation 228E. The rotatability of cantilever 224E may permit the cantilever 224E to rotate about one or more portions of the cantilever 224D. In some embodiments, one or more joints may connect the cantilever 224E to the cantilever 224D. The one or more joints may be pin joints, prismatic joints, ball joints, knuckle joints, cotter joints, or the like. In some embodiments, the joint between the cantilevers 224D and 224E may comprise one or more bolts, screws, or other affixing mechanisms to mechanically couple the cantilever 224E with the cantilever 224D. In some embodiments, the connection and/or movement relationship between the cantilever 224E and the cantilever 224D may be similar to or the same as the connection and/or movement relationship between the cantilever 224D and the cantilever 224C and/or the cantilever 224C and the cantilever 224B.

The cantilever 224E may comprise or be mechanically coupled with an end effector 230. The end effector 230 may be capable of gripping, holding, accepting, or otherwise mechanically couple with a surgical tool, such that the surgical tool is held in a stable position during use thereof. The surgical tool may be held by the end effector 230 during the course of a surgery or surgical procedure. The surgical tool may be a drill, reamer, saw, shaver, scalpel, tap, burr, combinations thereof, and/or the like. In some embodiments, the end effector 230 may be designed to accommodate and accept various tool sizes, shapes, and forms. For example, the end effector 230 may be configured to accept more than one type of tool (albeit not at the same time), where each surgical tool has a different distal end shape, but a similar proximal end shape.

The end effector 230 may be capable of rotating, translating, or otherwise moving with respect to an end effector axis 232. In some embodiments, the end effector axis 232 may run through the end effector 230 symmetrically, such that the end effector 230 may rotate without translating as shown in FIG. 2A. Additionally or alternatively, the end effector axis 232 may pass through one or more of the cantilevers 224A-224E and/or the shoulder 216, such that the end effector 230 is able to rotate and/or translate with respect to the one or more cantilevers 224A-224E and/or the shoulder 216.

The system 100 may comprise one or more inertial sensors 236 (or, more generally, one or more inertial measurement units 138) disposed in one or more locations of the robotic arm 116. In some embodiments, the inertial sensors 236 may be similar to or the same as the inertial sensors 142. As shown in FIG. 2A, the inertial sensors 236 may be disposed on the surgical bed 204, the attachment mechanism 206, the base 208, the shoulder 216, one or more of the cantilevers 224A-224E, and/or the end effector 230. The inertial sensor 236 may generate measurements (e.g., force measurements, pose changes, etc.) and provide such measurements to the system 100 and/or components thereof (e.g., the computing device 102, the processor 104, the database 130, etc.). The measurements may be used the by navigation system 118 to, for example, determine the poses of one or more components of the system 100 (e.g., the robotic arm 116 or components thereof, the shoulder 216, etc.) relative to one another or relative to a reference coordinate system (e.g., a patient coordinate system), as well as any change in pose of the one or more components of the system 100. In some embodiments, the inertial sensors 236 may be used to "zero" the system 100 or components thereof preoperatively (e.g., before a surgery or surgical procedure). In other words, the measurements from the inertial sensors 236 may be used to determine an equilibrium state, such as when the readings from the one or more inertial sensors 236 indicate that the components of the system 100 are no longer moving. The system 100 may use the zeroed pose as the initial pose during a surgery or surgical procedure, with departures from the initial pose being defined by the navigation system 118 as a change in pose.

In some embodiments, the inertial sensors 236 may be used to determine or verify the accuracy of one or more encoders or other sensors (not shown). For instance, the encoders may be disposed on or otherwise coupled with one or more components of the robot 114 (e.g., the robotic arm 116, the base 208, the height adjustment device 212, the shoulder 216, the end effector 230, etc.) such that the encoders measure when one or more components of the robot 114 changes pose. However, the encoders may fail to register a pose change for certain movements (e.g., deflections, bends, or other contouring of the component to which the encoder is attached or coupled), rendering the encoders inaccurate. The navigation system 118 may determine or verify the accuracy of the encoder by comparing readings generated by the inertial sensors 236 against readings generated by the encoders (or by comparing poses determined based on such readings).

Figure 2B:
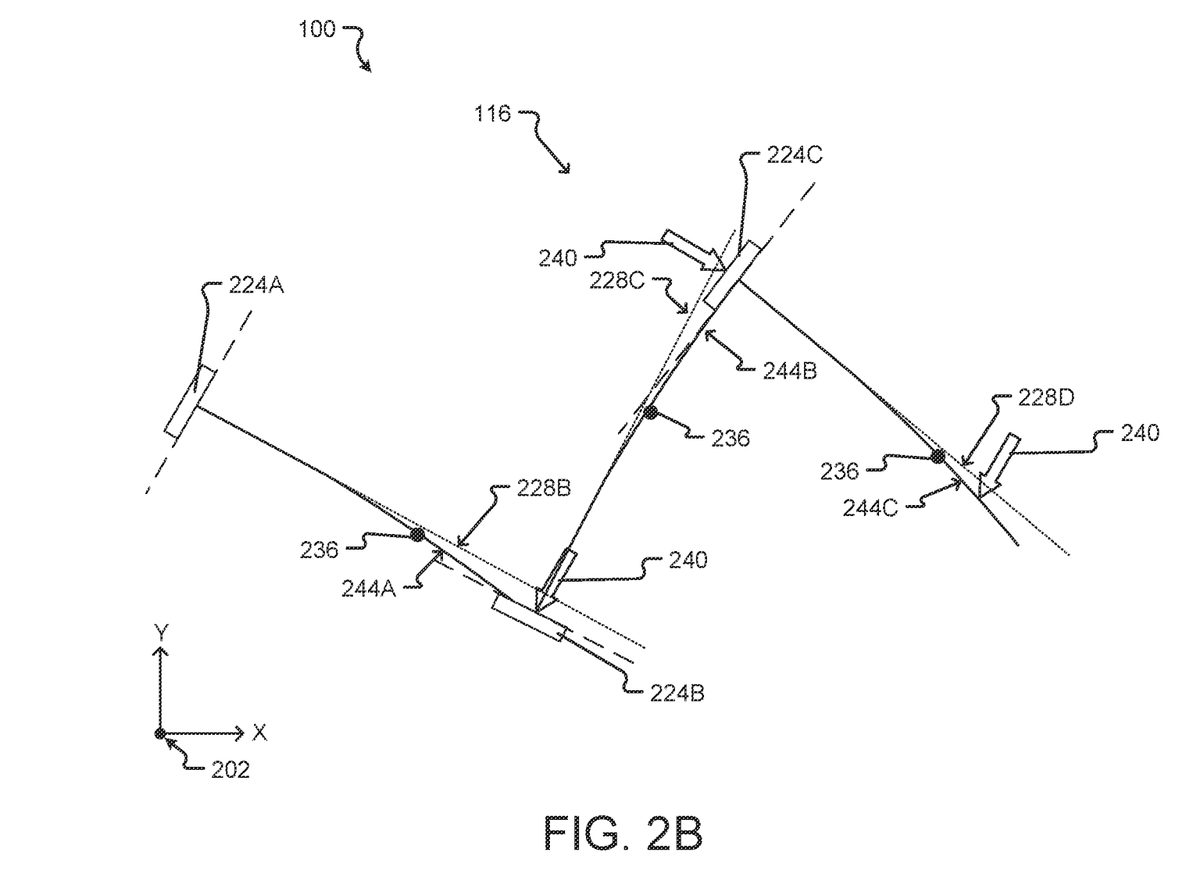
FIG. 2B is a schematic of deflections of the robotic arm according to at least one embodiment of the present disclosure.

During the course of a surgery or surgical procedure, the robotic arm 116 and/or components thereof (e.g., cantilevers 224A-224E, the end effector 230, etc.) may experience one or more forces. For instance, the robotic arm 116 may hold a surgical tool such as a drill, and may be used in a spinal surgery to hold a drill that drills into one or more vertebrae of the spine. As the drill operates, a force 240 may be generated by the drilling and may be applied to one or more portions of the robotic arm 116. For instance, the force 240 may be applied to a distal end 244C of the cantilever 224C. As depicted in FIG. 2B, the force 240 may displace the distal end 244C of the cantilever 224C, such that the cantilever 224C bends, deflects, or otherwise moves from a first position (where the cantilever 224C is aligned with the axis of rotation 228D) to a second position—where cantilever 224C is no longer aligned with the axis of rotation 228D. While FIG. 2B depicts the force 240 being applied to the cantilever 224C, the force 240 may additionally or alternatively be applied to the end effector 230 and/or the surgical tools attached thereto (e.g., a drill, a saw, a reamer, etc.).

Due to the connective or mechanically coupled nature of the cantilever 224C with the cantilever 224B, and of the cantilever 224B with the cantilever 224A, the force 240 may propagate through other portions of the robotic arm 116, such as through each of the cantilevers 224A-224C, the shoulder 216, the height adjustment device 212, and/or the base 208. Since the force 240 propagates through the cantilevers 224C and 224B, the force 240 respectively causes displacement of a distal end 244C and a distal end 244B. In FIG. 2B, the cantilever 224A may be fixed, and the propagation of the force 240 may cause a distal end 244A of the cantilever 224A to displace (e.g., bend, deflect, etc.) from the axis of rotation 228B. Since the force 240 causes each of the cantilevers 224B and 224C to move, the error associated with the difference between the expected or predetermined pose of each of the cantilevers 224A-224C and the actual pose of each of the cantilevers 224A-224C compounds. Further, the propagation of the force 240 causes not only angular deflection such that the cantilever is no longer aligned with the axis of rotation, but may additionally cause physical movement of the cantilevers 224A-224C and/or the surgical tool, resulting in multiplicative compound error of the actual pose of cantilever 224A and the pose known to the navigation system 118.

In some embodiments, the inertial sensors 236 may be disposed on each of the distal ends 244A-244C and may measure the force 240 and provide readings indicative of the magnitude and direction of the force 240. The navigation system 118 may use the readings to determine a change in pose of the cantilevers. In some embodiments, the navigation system 118 may use the readings to determine the second pose of each of the cantilevers (e.g., the pose after the force 240 has been applied to the cantilever 224D). For instance, the system 100 may use or implement a transformation 124 that transforms the measurements from the inertial sensors 236 to determine a pose of the cantilevers 224A-224C. The determined pose may be used by the navigation system 118 to determine a difference between the determined pose and the pose known to the navigation system 118 or the pose determined based on encoder readings; to determine or verify the accuracy of the encoder based on the determined difference; to adjust the registration of the robotic arm relative to the patient or to perform a new registration based on the determined pose; to navigate the robotic arm relative to the patient; to alert a surgeon that the force 240 exceeds a threshold value; combinations thereof; and/or the like.

Figure 3:
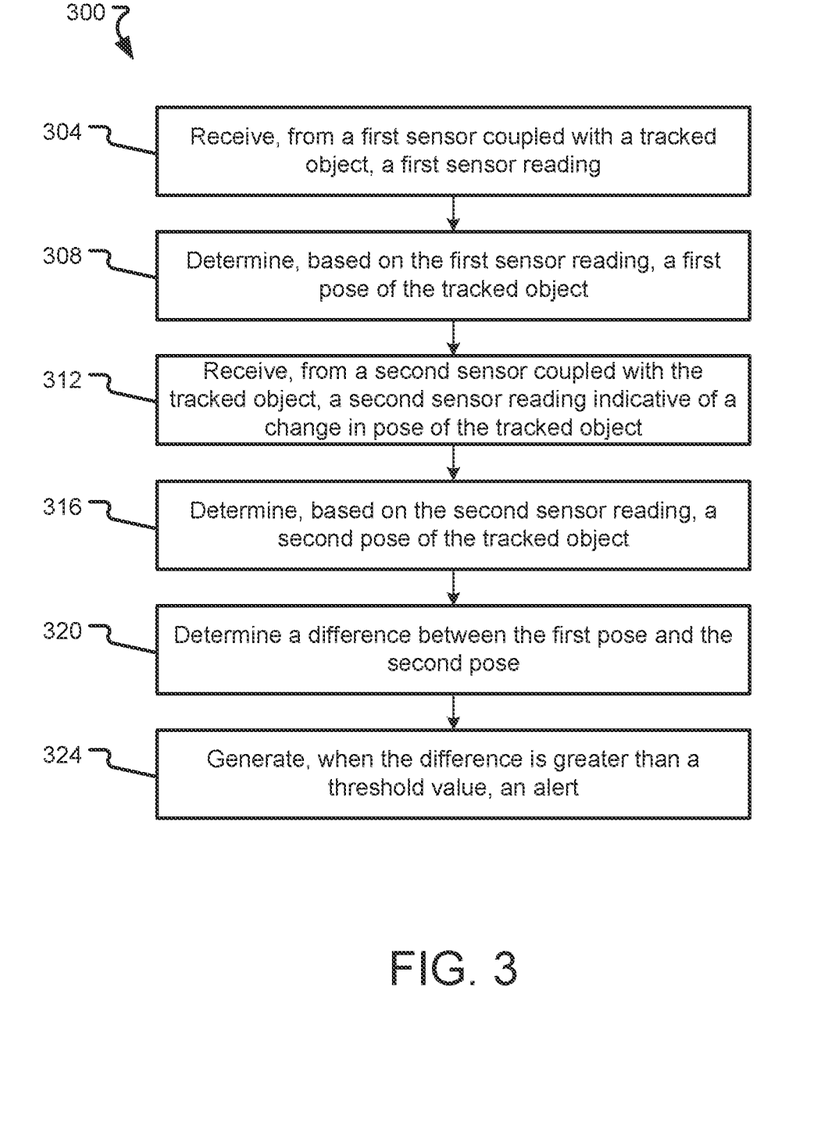
FIG. 3 is a flowchart according to at least one embodiment of the present disclosure.

FIG. 3 depicts a method 300 that may be used, for example, to determine a difference in pose of a tracked object.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The elements stored in the memory and executed by the processor may cause the processor to execute one or more steps of a function as shown in the method 300 described below. One or more portions of the method 200 may be performed by the processor executing any of the contents of memory, such as image processing 120, a comparison 122, a transformation 124, and/or a registration 128.

The method 300 comprises receiving, from a first sensor coupled with a tracked object, a first sensor reading (step 304). The tracked object may be a robotic arm 116, portions of the surgical bed 204, an attachment mechanism 206, a base 208, a height adjustment device 212, a shoulder 216, cantilevers 224A-224E, an end effector 230 (and/or a surgical tool gripped by or otherwise coupled with the end effector 230), combinations thereof, and/or the like. In some embodiments, the first sensor may be or comprise an encoder, which may track the dead reckoning position of the tracked object. For example, the encoder may be attached to or disposed on a cantilever (e.g., a cantilever 224A), and may provide a first sensor reading that comprises information indicative of a pose of the cantilever in a first coordinate system (e.g., a coordinate system 202). The encoder may be or comprise a linear encoder and/or a rotary encoder.

The method 300 also comprises determining, based on the first sensor reading, a first pose of the tracked object (step 308). The step 308 may use content stored in the memory 106 that performs transformations 124, which may take at least the first sensor reading as an input and output a first pose of the tracked object as an output. For instance, the first sensor reading may comprise information related to an encoder value, and the transformation 124 may use the encoder value, as well as information related to the coordinate system in which the encoder resides, to generate the first pose of the tracked object. In some embodiments, the first pose of the tracked object may be a pose before beginning a surgery or surgical procedure (e.g., a preoperative pose), such that the navigation system 118 has information about the pose of the tracked object before the surgery or surgical procedure. In such embodiments, the initial pose may be a desired pose, such as a pose determined or required by a surgical plan.

The method 300 also comprises receiving, from a second sensor coupled with the tracked object, a second sensor reading indicative of a change in pose of the tracked object (step 312). The second sensor may be or comprise an inertial measurement unit 138 and/or an inertial sensor 236 that is coupled with the tracked object (e.g., disposed on the tracked object, disposed proximate the tracked object, disposed a first distance from the tracked object, etc.) and capable of measuring the change in pose of the tracked object. The measured change may be captured or reflected in the second sensor reading. For instance, the inertial sensor 236 may be disposed on the tracked object and, when the tracked object moves, an internal gyroscope of the inertial sensor 236 measures the movement of the tracked object and outputs the second sensor reading. In another example, the inertial measurement unit 138 may include a force sensor that measures a force 240 on the tracked object, and provides information related to the magnitude and direction of the force in the second sensor reading. In some embodiments, the movement of the tracked object reflected in the second sensor reading may be caused, for example, by the operation of a surgical tool, such as a surgical tool held by the robotic arm 116 and operated autonomously or semi-autonomously by a navigation system 118 and/or a user (e.g., a surgeon).

The second sensor reading may be or comprise information related to the force 240 that acts on the tracked object. For instance, the force 240 may be a force generated by a surgical tool drilling into a vertebra of a patient, with the force 240 causing movement of the cantilever 224E (which may be or comprise the tracked object) that is mechanically coupled with the surgical tool through the end effector 230. In such embodiments, the second sensor may be disposed proximate to, on, or a predetermined distance from the cantilever 224E, and may detect the force 240 and/or the movement of the cantilever 224E and produce the second sensor reading comprising information related thereto. In other embodiments, the force 240 may be an additional or alternative force generated by the user (e.g., the surgeon leans on the surgical bed 204 or some other component of the robotic arm 116). In such embodiments, the second sensor reading may comprise information related to the force generated by the user.

The method 300 also comprises determining, based on the second sensor reading, a second pose of the tracked object (step 316). The step 316 may use or implement content stored in the memory 106 that performs one or more transformations 124 that transform the second sensor reading and the first pose information to determine the second pose. In some embodiments, the transformation 124 may receive the first pose information and may use the second sensor reading to determine a change in pose of the first pose from the first pose to the second pose. In some embodiments, the second sensor reading may be related to a force on the tracked object (e.g., the force 240 on the cantilever 224E), with the second sensor reading providing information indicative of the location of the force and the magnitude and direction of the force on the tracked object; the transformation 124 may use this information, along with the first pose information, to determine new coordinates describing the second pose of the tracked object. In some embodiments, the output of the transformation 124 may be stored in a database 130.

The method 300 also comprises determining a difference between the first pose and the second pose (step 320). The step 320 may use or implement content stored in the memory 106 that performs one or more comparisons 122 that compare the first pose of the tracked object with the second pose of the tracked object to determine the difference therebetween. For example, the comparison 122 may use coordinates associated with the first pose of the tracked object and coordinates associated with the second pose, and determine the difference between the values of the coordinates. In some embodiments, the coordinates associated with the first and second poses may be passed through content stored in the memory 106 that performs one or more registrations 128 before being compared. The registration 128 may map the coordinates associated with the tracked object in the first pose and the coordinates associated with the tracked object in the second pose into a common coordinate system (e.g., mapping the first pose's coordinates into the second pose's coordinate system (or vice versa), mapping both sets of coordinates into a patient coordinate system, etc.). In some embodiments, the determined difference between the first pose and the second pose of the tracked object may be saved (e.g., in the database 130). Additionally or alternatively, the determined difference may be rendered to a user interface, such as a user interface 110.

The method 300 also comprises generating, when the difference is greater than a threshold value, an alert (step 324). The step 324 may use one or more components of the system 100 (e.g., a processor 104) to determine when the difference between the first pose of the tracked object and the second pose of the tracked object is greater than a threshold value. The threshold value may be a quantitative indicator (e.g., a percent, an integer, etc.) over which the navigation system 118 or other component of the system 100 determines that the difference is unacceptable and/or that the tracked object should be adjusted. For instance, the threshold value may be 1%, which may indicate that any pose difference greater than 1% will cause the alert to be triggered. In some embodiments, the threshold value may be a safety threshold, such that any value above the threshold value may introduce safety concerns regarding the surgery or surgical procedure. As an example, the tracked object may be surgical tool, and the navigation system 118 or component of the system 100 may have a threshold value of 1%. The threshold value of 1% may indicate that the navigation system 118 cannot tolerate a surgical tool pose difference of greater than 1% since such a pose difference may create too high a risk for the patient (e.g., the pose difference may mean the surgical tool is operating in the incorrect location) and/or may otherwise lead to patient or surgeon dissatisfaction (e.g., the pose difference may make it difficult for the surgeon to operate the surgical tool).

The alert may be or comprise visual (e.g., a flashing light, text displayed on the user interface 110), audio (e.g., a warning siren, a beep, and/or any other audible alert), and/or tactile alert (e.g., a buzzing of one or more surgical instruments) that may indicate to users in the surgical environment (e.g., surgeons, surgical staff, etc.) that the threshold value has been exceeded. In some embodiments, the alert may be provided partially or fully via the user interface 110.

The present disclosure encompasses embodiments of the method 300 that comprise more or fewer steps than those described above, and/or one or more steps that are different than the steps described above.

Figure 4:
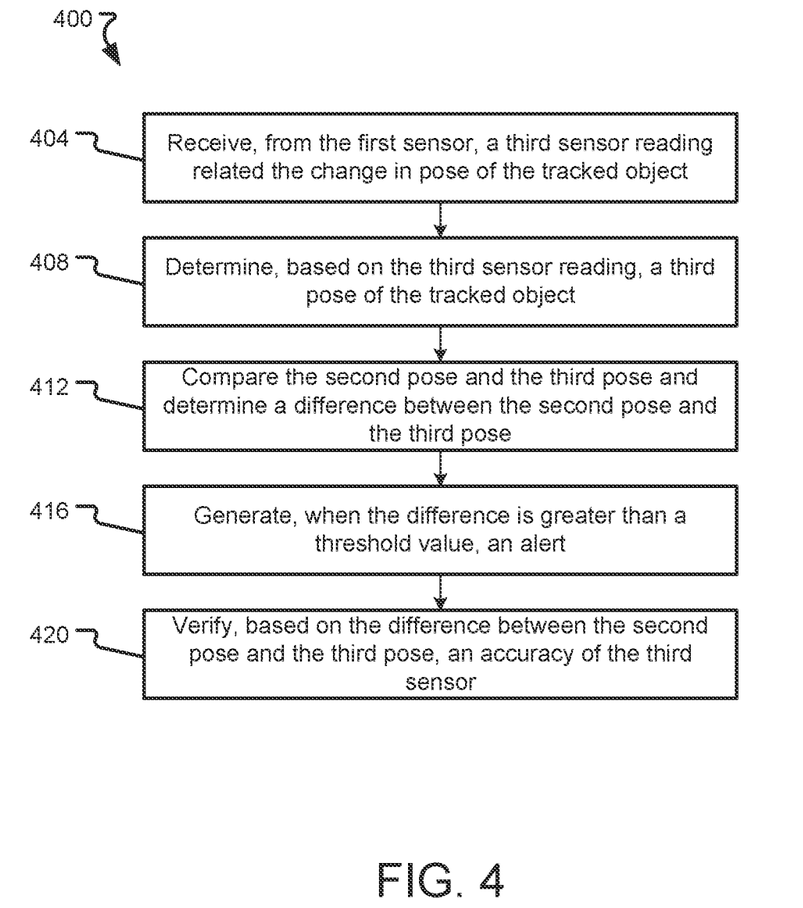
FIG. 4 is a flowchart according to at least one embodiment of the present disclosure.

FIG. 4 depicts a method 400 that may be used, for example, to verify the accuracy of a sensor based on a pose difference.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The elements stored in the memory and executed by the processor may cause the processor to execute one or more steps of a functions as shown in the method 400 described below. One or more portions of the method 200 may be performed by the processor executing any of the contents of memory, such as image processing 120, a comparison 122, a transformation 124, and/or a registration 128.

The method 400 comprises receiving, from the first sensor, a third sensor reading related to the change in pose of the tracked object (step 404). In some embodiments, the step 404 may continue from the step 320. In other words, a computing device 102, processor 104, navigation system 118, or other component of the system 100 may have performed the method 300 (e.g., using a processor 104) and have first and second pose information. The third sensor may be or comprise an encoder (such as any encoder previously discussed or mentioned herein) disposed proximate to or on the tracked object and may provide the third sensor reading related to the change in the tracked object from the first pose to the second pose. In some embodiments, the third sensor may provide the third sensor reading simultaneously or near-simultaneously (e.g., within 1 millisecond (ms), within 5 ms, within 100 ms, within 1 second (s), within 5s, etc.) with the second sensor providing the second sensor reading. The third sensor reading may be or comprise information related to the change in pose of the tracked object (e.g., coordinate change information, information describing new coordinates of the tracked object after the change of pose, etc.).

The method 400 also comprises determining, based on the third sensor reading, a third pose of the tracked object (step 408). The step 408 may use or implement one or more transformations 124, which may use the third sensor reading and transform the reading into the third pose of the tracked object. For example, the third sensor reading may comprise information related to an encoder value, and the transformation 124 may use the encoder value, as well as information related to the coordinate system in which the encoder resides, to generate the third pose of the tracked object. In some embodiments, the third pose may be determined independently of the second pose. In other words, the third pose may be based on the third sensor reading (which is generated by the third sensor) without taking into account any information related to the second sensor reading or the second pose determined therefrom. Similarly, the second pose may be determined based on the second sensor reading (which is generated by the second sensor) without taking into account any information related to the third sensor reading or the third pose determined therefrom.

The method 400 also comprises comparing the second pose to the third pose and determining a difference between the second pose and the third pose (step 412). The second pose may be related to the ending pose of the tracked object after the tracked object has changed pose from the first pose as determined based on information provided by the second sensor (e.g., an inertial sensor 236), while the third pose is related to the ending pose of the tracked object after the tracked object has changed pose from the first pose as determined based on information provided by the third sensor (e.g., an encoder). In some embodiments, the second pose and the third pose may be the same, which may indicate that both the second sensor and the third sensor determined the same movement of the tracked object.

In some embodiments, however, if movements of the tracked object are inaccurately captured by second sensor or third sensor (e.g., an encoder fails to accurately capture information related to the change of pose), the second pose may be different from the third pose. In some embodiments, the step 412 may use or implement one or more comparisons 122 that may take the second pose and the third pose as inputs, and output a difference therebetween. In some embodiments, the comparison 122 may output a difference between one or more coordinates associated with the tracked object in the second pose and one or more coordinates associated with the tracked object in the third pose. In some embodiments, the coordinates associated with the second and third poses may be passed through one or more registrations 128 before being used in the comparison 122. The registration 128 may map the coordinates associated with the tracked object in the second pose and the coordinates associated with the tracked object in the third pose into a common coordinate system (e.g., mapping the second pose's coordinates into the third pose's coordinate system (or vice versa), mapping both sets of coordinates into a patient coordinate system, etc.). In some embodiments, the determined difference between the second pose and the third pose of the tracked object may be saved (e.g., in the database 130).

Additionally or alternatively, the determined difference may be rendered to a user interface, such as a user interface 110.

The method 400 also comprises generating, when the difference is greater than a threshold value, an alert (step 416). The step 416 may be similar to or the same as the step 324. For instance, the alert may be rendered to a user interface 110, such that users in a surgical environment (e.g., surgeons, surgical staff, etc.) may view the difference between the second pose and the third pose.

The method 400 also comprises verifying, based on the difference between the second pose and the third pose, an accuracy of the third sensor (step 420). In some embodiments, the navigation system 118 may use the second sensor reading and determined second pose of the tracked object as the "real" final pose of the tracked object (e.g., the navigation system 118 may treat the second pose as the actual pose of the tracked object after the tracked object changes pose) and may use the difference in poses to determine or otherwise verify the accuracy of the third sensor. For example, the second sensor may be an inertial sensor capable of detecting forces on the tracked object that the third sensor (e.g., an encoder) cannot detect. As such, the navigation system 118 may use or define the readings of the second sensor (and poses determined based thereon) as the actual pose of the tracked object in the surgical environment. The navigation system 118 may use the second sensor readings and second sensor pose to check the accuracy of the third sensor.

In some embodiments, the navigation system 118 may use the threshold value of the step 416 as a criterion for the accuracy of the third sensor. For instance, the threshold value may be 1% (e.g., a 1% difference between the second pose and the third pose), and the navigation system 118 may determine, when the difference is greater than 1%, that the third sensor is not providing an accurate third sensor reading. In some embodiments, the second sensor may detect the change in pose of the tracked object from the first pose to the second pose, while the third sensor may fail to accurately detect a change in pose (e.g., the third sensor reading does not indicate that the tracked object has moved from the first pose). In such embodiments, the third pose may be the same as the first pose, while the second pose is different from the third pose and the first pose. Hence, the navigation system 118 may determine, when the difference in poses is greater than the 1% threshold value, that the third sensor is malfunctioning and/or is incapable of providing an accurate third sensor reading. In some embodiments, the navigation system 118 may render an alert to the user interface 110 indicating that the third sensor is malfunctioning, inaccurate, or otherwise incapable of correctly capturing pose changes.

The present disclosure encompasses embodiments of the method 400 that comprise more or fewer steps than those described above, and/or one or more steps that are different than the steps described above.

Figure 5:
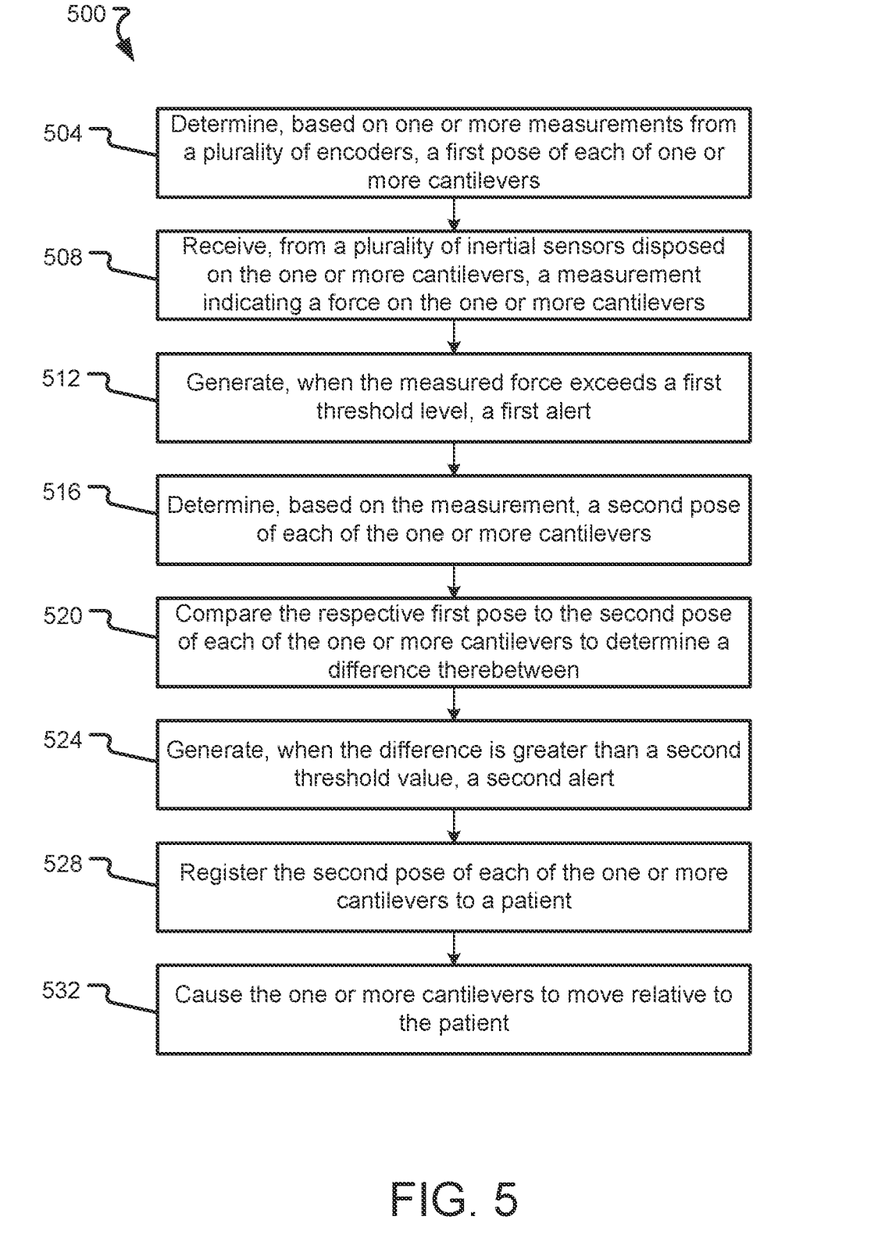
FIG. 5 is a flowchart according to at least one embodiment of the present disclosure.

FIG. 5 depicts a method 500 that may be used, for example, to determine the pose of one or more cantilevers experiencing a force thereon.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The elements stored in the memory and executed by the processor may cause the processor to execute one or more steps of a function as shown in the method 500 described below. One or more portions of the method 200 may be performed by the processor executing any of the contents of memory, such as image processing 120, a comparison 122, a transformation 124, and/or a registration 128.

The method 500 comprises determining, based on one or more measurements from a plurality of encoders, a first pose of each of one or more cantilevers (step 504). The plurality of encoders may be disposed on one or more cantilevers 224A-224E, or otherwise coupled therewith to measure the movement of the one or more cantilevers. While the method 500 is generally discussed with respect to the movement of the one or more cantilevers 224A-224E, it is to be understood that the plurality of encoders may be disposed on additional or alternative components of the system 100, such as the surgical bed 204, the attachment mechanism 206, the base 208, the height adjustment device 212, the shoulder 216, the end effector 230, combinations thereof, and/or the like.

The plurality of encoders may be or comprise linear and/or rotary encoders and may provide signals indicative of movement associated with the cantilevers 224A-224E. The encoders may generate the one or more measurements that are used by the navigation system 118 to determine the pose of each of the one or more cantilevers 224A-224E. For instance, each of the cantilevers 224A-224E may comprise one or more of the plurality of the encoders, such that the movement of each cantilever 224A-224E is captured in information created by the one or more measurements. In some embodiments, the one or more measurements may be stored in a database 130. The step 504 may use or implement one or more transformations 124 that may receive the one or more measurements as inputs and output the first pose of each of the one or more cantilevers 224A-224E. In some embodiments, the first pose of each of the one or more cantilevers 224A-224E may be a preoperative pose (e.g., a pose determined before a surgery or surgical procedure).

The method 500 also comprises receiving, from a plurality of inertial sensors disposed on the one or more cantilevers, a measurement indicating a force one the one or more cantilevers (step 508). The plurality of inertial sensors may each be similar to or the same as an inertial sensor 142 or an inertial sensor 236. Each inertial sensor of the plurality of inertial sensors may comprise one or more gyroscopes, accelerometers, magnetometers, combinations thereof, and/or the like to detect inertial movements of the inertial sensor (and, by extension, any object to which the inertial sensor is attached). In some embodiments, the plurality of sensors may be packaged in an inertial measurement unit such as an inertial measurement unit 138. In some embodiments, the plurality of inertial sensors may comprise one or more force sensors, which may be capable of measuring the force acting on the one or more cantilevers. In such embodiments, the measurement received by the step 508 may be or comprise information related to force measured by the one or more force sensors. In other embodiments, the plurality of inertial sensors may comprise one or more force sensors that generate readings that enable the navigation system 118 to determine the force on the one or more cantilever (e.g., the readings provide different position measurements at different times, allowing the system to calculate the force that caused the plurality of inertial sensors to move).

The force may be similar to or the same as a force 240 and may be applied to or against the one or more cantilevers 224A-224E. For example, the force 240 may be a force generated when a surgical tool held by an end effector 230, such as a drill, begins to drill into a vertebra of a patient during a spine surgery or spinal surgical procedure. As the surgical tool drills into the vertebra, the vertebra may exert a resistive force on the surgical tool. The resistive force may be propagated back through the end effector 230. Similarly, and due to the mechanical coupling of the end effector 230 with the robotic arm 116, the force 240 may also propagate through the cantilevers 224A-224E connected to the end effector 230. As the force 240 is propagated through the cantilevers 224A-224E and the end effector 230, each of the cantilevers 224A-224E and/or the end effector 230 may experience a deflection, bending, or other displacement due to the force. In some embodiments, the force 240 may be generated due to gravity or any other force not directly related to the surgery or surgical procedure. For instance, the force 240 may be caused by gravity acting on a locked cantilever, with the force causing the cantilever to bend or otherwise be displaced from a desired pose.

The method 500 also comprises generating, when the measured force exceeds a first threshold value, a first alert (step 512). The measured force may be directly measured (e.g., by a force sensor) or determined (e.g., using positional data generated by the plurality of inertial sensors in content stored in the memory 106) and compared with the first threshold value. In some embodiments, the first threshold value may be a predetermined quantitative indicator (e.g., a percent value, an integer, etc.) related to the safety or stability of or required by the system 100 (or components thereof such as the navigation system 118); for instance, the first threshold value may be 1 Newton (N), which may indicate that any force generated on the cantilever that exceeds 1 N is deemed unsafe or unacceptable by, for example, the navigation system 118 (e.g., a force of greater than 1 N may risk moving the robotic arm 116 enough to change the angle of drilling of a surgical tool attached thereto). The value of 1 N is in no way limiting, and the first threshold value may be predetermined or otherwise chosen based on, for example, the type of surgery, the type of surgical equipment used for the surgery, the type of surgeon, the duration of the surgery, the number of sections or cantilevers of the surgical arm, combinations thereof, and/or the like. For instance, the first threshold value may be a larger value when the robotic arm comprises two cantilevers than when the robotic arm comprises five or more cantilevers. As another example, the first threshold value may be smaller when the robotic arm is performing or assisting in the performance of drilling into a vertebra than when the robotic arm is performing or assisting in cutting soft tissue.

In some embodiments, step 512 may use one or more comparisons 122 that take the measured force and the first threshold values and generate a binary value. For example, a value of "1" may indicate that the measured force exceeds the first threshold value, while a value of "0" may indicate that the measured force does not exceed the first threshold value (or vice versa). In some embodiments, the binary value may be used by the navigation system 118 generate the first alert. In other words, a value of "1" may cause the system 100 to generate the first alert, while the navigation system 118 may remain idle or otherwise abstain from sending the first alert when a value of "0" is received. The first alert may be a visual, audial, or tactile signal that alerts users in the surgical environment (e.g., a surgeon, surgical staff, etc.) that the measured force exceeds the first threshold value. In some embodiments, the output of the alert may be similar to the alert of step 324. For instance, the alert may be a visual alert rendered to a user interface such as the user interface 110. In some embodiments, a binary value may be returned for each cantilever.

Additionally or alternatively, the navigation system 118 may cause the surgery or surgical procedure to pause or stop when the first threshold value is exceeded. The exceeding of the first threshold value may indicate that the force experienced by the surgical robot (or components thereof) is too high, which may indicate that the current operation of the surgical robot is dangerous or undesired. In some embodiments, the navigation system 118 may deactivate an operation of the surgical tool (e.g., turning off a drill attached to the end effector 230) until the first threshold value is no longer exceeded.

The method 500 also comprises determining, based on the measurement, a second pose of each of the one or more cantilevers (step 516). The force 240 may cause the one or more cantilevers 224A-224E to bend, deflect, or otherwise move from the first pose to the second pose. The measurement of the force 240 may be used by the step 516 to determine the second pose of each of the one or more cantilevers 224A-224E. The step 516 may use or implement content of the memory 106 to perform one or more transformations 124 that may take the first pose of each of the one or more cantilevers 224A-224E and the force 240 and may transform the data to determine and output the second pose of each of the one or more cantilevers 224A-224E as an output. In some embodiments, the step 516 may be similar to or the same as the step 316.

The method 500 also comprises comparing the respective first pose to the second pose of each of the one or more cantilevers to determine a difference therebetween (step 520). In some embodiments, the step 520 may use or implement content of the memory 106 to enable one or more comparisons 122 that may take the first pose and the second pose of each of the cantilevers 224A-224E as inputs and output the difference between the first pose and the second pose of the cantilevers 224A-224E. In some embodiments, the step 520 may be similar to or the same as the step 320 or the step 412. In some embodiments, the comparisons 122 may output a difference for each of the cantilevers 224A-224E.

The method 500 also comprises generating, when the difference is greater than a second threshold value, a second alert (step 524). The step 524 may be similar to or the same as the step 324 or the step 416. In some embodiments, the second threshold value may be similar to or the same as the threshold value of the step 324. In some embodiments, the second alert may be similar to or the same as the first alert of the step 512 or the alert of the step 324.

In some embodiments, each difference between each of the cantilevers 224A-224E may be received by the navigation system 118. In such embodiments, the navigation system 118 may compare each difference for each of the cantilevers 224A-224E to the second threshold value and generate the second alert when at least one of the differences exceeds the second threshold value. In other embodiments, the navigation system 118 may only generate the second alert when each of the differences in pose exceeds the second threshold value.

The method 500 also comprises registering the second pose of each of the one or more cantilevers to a patient (step 528). The step 528 may use or implement content from the memory 106 to perform one or more registrations 128 that take the second pose of the one or more cantilevers and information related to the pose of the patient as inputs and may output a registration that maps the coordinates of the one or more cantilevers in a coordinate system associated with the patient (or alternatively a registration that maps coordinates associated with the patient into a coordinate system associated with the one or more cantilevers). In some embodiments, the registrations 128 may map both coordinates of the one or more cantilevers and the coordinates of the patient into a common third coordinate system (e.g., a coordinate system associated with the surgical environment).

The method 500 also comprises causing the one or more cantilevers to move relative to the patient (step 532). The step 532 may be carried out by the navigation system 118 or other components of the system 100, which may cause the one or more cantilevers (or, more generally, the robotic arm) to move relative to the patient. In some embodiments, the movement may be based on a surgical plan. In some embodiments, the navigation system 118 may cause the robotic arm to move such that the cantilevers whose movement (e.g., bend, deflection, etc.) exceeded the threshold value are caused to move relative to the patient, while the remaining cantilevers whose movement did not exceed the threshold value are kept in place.

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 3, 4, and 5 (and the corresponding description of the methods 300, 400, and 500), as well as methods that include additional steps beyond those identified in FIGS. 3, 4, and 5 (and the corresponding description of the methods 300, 400, and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system, comprising:
a processor; and
at least one inertial sensor having a known physical relationship with a tracked object in a first pose, the at least one inertial sensor providing a measurement indicative of a movement of the tracked object from the first pose to a second pose,
wherein the processor determines the second pose of the tracked object based on the measurement provided by the at least one inertial sensor and a second measurement provided by one or more encoders positioned on or within the tracked object.

2. The system of claim 1, wherein the movement of the tracked object is caused by a force applied to the tracked object, and wherein the processor determines a difference between the first pose and the second pose.

3. The system of claim 2, wherein the processor generates, when the difference between the first pose and the second pose is greater than a threshold value, an alert.

4. The system of claim 1, wherein the tracked object comprises a robot, and wherein the at least one inertial sensor comprises a plurality of sensors disposed on one or more locations of the robot.

5. The system of claim 4, wherein the one or more locations of the robot comprise at least one of one or more joints of the robot, one or more cantilevers of the robot, a height adjustment device mechanically coupled with the robot, and a shoulder of the robot.

6. The system of claim 4, wherein the robot comprises a plurality of cantilevers, and wherein the movement of the robot from the first pose to the second pose comprises at least one cantilever of the plurality of cantilevers deflecting from a first position to a second position.

7. The system of claim 1, wherein the at least one inertial sensor comprises a force sensor, and wherein the force sensor measures a force on the tracked object.

8. A system, comprising:
a processor,
a tracked object oriented in a first pose; and
an inertial measurement unit disposed in a known physical relation to the tracked object, the inertial measurement unit producing a first reading indicating a change in pose of the tracked object, wherein the processor determines a second pose of the tracked object based at least in part on the first reading provided by the inertial measurement unit and a second reading provided by one or more encoders positioned on or within the tracked object.

9. The system of claim 8, wherein the second reading provided by the one or more encoders is independent of the first reading.

10. The system of claim 9, wherein the processor determines a third pose of the tracked object based on the second reading from the one or more encoders, and wherein the processor determines a difference between the second pose to the third pose.

11. The system of claim 10, wherein the processor generates, when the difference between the second pose and the third pose exceeds a threshold value, an alert, and wherein the processor verifies, when the difference between the second pose and the third pose exceeds the threshold value, an accuracy of the one or more encoders.

12. The system of claim 8, wherein the inertial measurement unit is disposed on the tracked object, wherein the inertial measurement unit comprises a force sensor, and wherein the inertial measurement unit generates a third reading measuring a force on the tracked object.

13. The system of claim 12, wherein the processor generates, when the measured force exceeds a threshold value, an alert.

14. The system of claim 13, wherein the tracked object comprises a cantilever, and wherein the force is applied to one or more portions of the cantilever.

15. A method, comprising:
receiving, from a first sensor coupled with a tracked object, a first sensor reading;
determining, based at least in part on the first sensor reading, a first pose of the tracked object;
receiving, from a second sensor coupled with the tracked object, a second sensor reading indicating the tracked object has changed pose from the first pose to a second pose;
receiving, from the first sensor, a third sensor reading related to the change in pose of the tracked object; and
determining, based on the second sensor reading and the third sensor reading, a third pose of the tracked object.

16. The method of claim 15, wherein the first sensor comprises an encoder, wherein the second sensor comprises a plurality of inertial sensors disposed on one or more locations of the tracked object, and wherein determining the third pose of the tracked object further comprises:
determining, based on the third sensor reading, a fourth pose of the tracked object;
comparing the second pose to the fourth pose; and
determining, based on the comparison of the second pose to the fourth pose, a difference between the second pose and the fourth pose.

17. The method of claim 16, further comprising:
generating, when the difference between the second pose and the fourth pose is above a first threshold value, a first alert; and
verifying, based on the difference between the second pose and the fourth pose, an accuracy of the encoder.

18. The method of claim 17, wherein the tracked object comprises a robot having a first cantilever, wherein the change in pose of the robot is caused at least in part by a force applied to the first cantilever to cause the first cantilever to move from a first position to a second position, and wherein the method further comprises:
receiving, from a force sensor, a measurement of the force on the first cantilever; and
generating, when the force on the first cantilever exceeds a second threshold value, a second alert.

19. The method of claim 17, wherein the tracked object comprises a robotic arm, and wherein the method further comprises:
registering, based on the third pose, one or more portions of the robotic arm to a patient; and
causing, based on the registration, the robotic arm to move relative to the patient.

20. The method of claim 16, wherein the one or more locations comprises at least one of one or more joints of a robot, a height adjustment device mechanically coupled to the robot, one or more cantilevers of the robot, and a shoulder of the robot.

* * * * *